(12) United States Patent
Brand et al.

(10) Patent No.: US 9,232,935 B2
(45) Date of Patent: *Jan. 12, 2016

(54) HANDLE FOR ACTUATING A DEVICE

(75) Inventors: Marc I. Brand, Deerfield, IL (US);
David Stienmier, Arvada, CO (US);
Kenneth W. Maydew, Niwot, CO (US)

(73) Assignee: Misder, LLC, Niwot, CO (US)

( * ) Notice: Subject to any disclaimer, the term of this patent is extended or adjusted under 35 U.S.C. 154(b) by 678 days.

This patent is subject to a terminal disclaimer.

(21) Appl. No.: 13/195,542

(22) Filed: Aug. 1, 2011

(65) Prior Publication Data

US 2013/0035671 A1    Feb. 7, 2013

(51) Int. Cl.
| | | |
|---|---|---|
| *A61B 17/00* | (2006.01) | |
| *A61B 1/12* | (2006.01) | |
| *A61B 1/00* | (2006.01) | |
| A61B 17/22 | (2006.01) | |
| A61B 17/29 | (2006.01) | |
| A61B 17/34 | (2006.01) | |
| A61B 19/00 | (2006.01) | |

(52) U.S. Cl.
CPC ....... *A61B 17/00234* (2013.01); *A61B 1/00131* (2013.01); *A61B 1/126* (2013.01); *A61B 2017/0046* (2013.01); *A61B 2017/00464* (2013.01); *A61B 2017/22072* (2013.01); *A61B 2017/2911* (2013.01); *A61B 2017/2918* (2013.01); *A61B 2017/3445* (2013.01); *A61B 2019/304* (2013.01); *A61B 2019/343* (2013.01)

(58) Field of Classification Search
CPC ............ A61M 5/3271; A61M 5/3243; A61M 25/0612; A61M 25/0618; A61B 17/00234; A61B 1/00131; A61B 1/126
USPC ....................................... 606/1; 604/192–198
See application file for complete search history.

(56) References Cited

U.S. PATENT DOCUMENTS

| | | |
|---|---|---|
| 3,145,249 A | 8/1964 | Meltzer |
| 4,856,518 A | 8/1989 | McFadden |
| 4,919,113 A | 4/1990 | Sakamoto et al. |
| 5,135,530 A | 8/1992 | Lehmer |
| 5,274,874 A | 1/1994 | Cercone et al. |
| 5,295,952 A | 3/1994 | Pietrafitta |
| 5,313,934 A | 5/1994 | Wiita et al. |

(Continued)

OTHER PUBLICATIONS

Supplementary Partial European Search Report prepared by the European Patent Office in European Patent Application 12819741.5, completed Mar. 5, 2015.

(Continued)

*Primary Examiner* — William Thomson
*Assistant Examiner* — John R Downey
(74) *Attorney, Agent, or Firm* — McDonnell Boehnen Hulbert & Berghoff LLP

(57) ABSTRACT

This disclosure may disclose, inter alia, a handle for actuating a device. The handle may include a top comprising a first end and a second end, a first top side coupled to the first end of the top via a first corner hinge, and a second top side coupled to the second end of the top via a second corner hinge. The handle may further include a first bottom side coupled to the first top side via a first side hinge, a second bottom side coupled to the second top side via a second side hinge, and a bottom coupled to the first bottom side via a third corner hinge and coupled to the second bottom side via a fourth corner hinge. In some examples, actuation of the handle may cause deployment or retraction of an element from or into a shaft.

31 Claims, 11 Drawing Sheets

(56) References Cited

U.S. PATENT DOCUMENTS

| | | | |
|---|---|---|---|
| 5,382,297 | A | 1/1995 | Valentine et al. |
| 5,400,767 | A | 3/1995 | Murdoch |
| 5,464,008 | A | 11/1995 | Kim |
| 5,492,766 | A | 2/1996 | Howard et al. |
| 5,514,082 | A | 5/1996 | Smith, III |
| 5,514,084 | A | 5/1996 | Fisher |
| 5,647,840 | A | 7/1997 | D'Amelio et al. |
| 5,654,824 | A | 8/1997 | Tarr et al. |
| 5,951,525 | A | 9/1999 | Thorne et al. |
| 6,126,592 | A | 10/2000 | Proch et al. |
| 6,354,992 | B1 | 3/2002 | Kato |
| 6,409,657 | B1 | 6/2002 | Kawano |
| 6,447,446 | B1 | 9/2002 | Smith et al. |
| 6,447,466 | B1 | 9/2002 | Smith |
| 6,575,204 | B1 | 6/2003 | Godfrey et al. |
| 6,699,331 | B1 | 3/2004 | Kritzler |
| 6,755,782 | B2 | 6/2004 | Ogawa |
| 6,986,759 | B1 | 1/2006 | Jeremijevic |
| 2003/0149404 | A1 | 8/2003 | Lehmann |
| 2003/0181871 | A1 | 9/2003 | Wilkinson et al. |
| 2006/0293559 | A1 | 12/2006 | Grice et al. |
| 2007/0118074 | A1 | 5/2007 | Dario et al. |
| 2009/0105543 | A1 | 4/2009 | Miller et al. |

OTHER PUBLICATIONS

Endoscope Video Adaptors & Measurement Instrumentations Products, http://www.lighthouseoptics.com/medical-optics-products?c=7&p=32, printed from Internet on Aug. 1, 2011.

Product Showcase: Minimally Invasive Surgery Products, www.surgicalproductsmag.com, Apr. 2010.

International Search Report and Written Opinion prepared by the Korean Patent Office in International Patent Application PCT/US2012/048762, mailed Feb. 13, 2013.

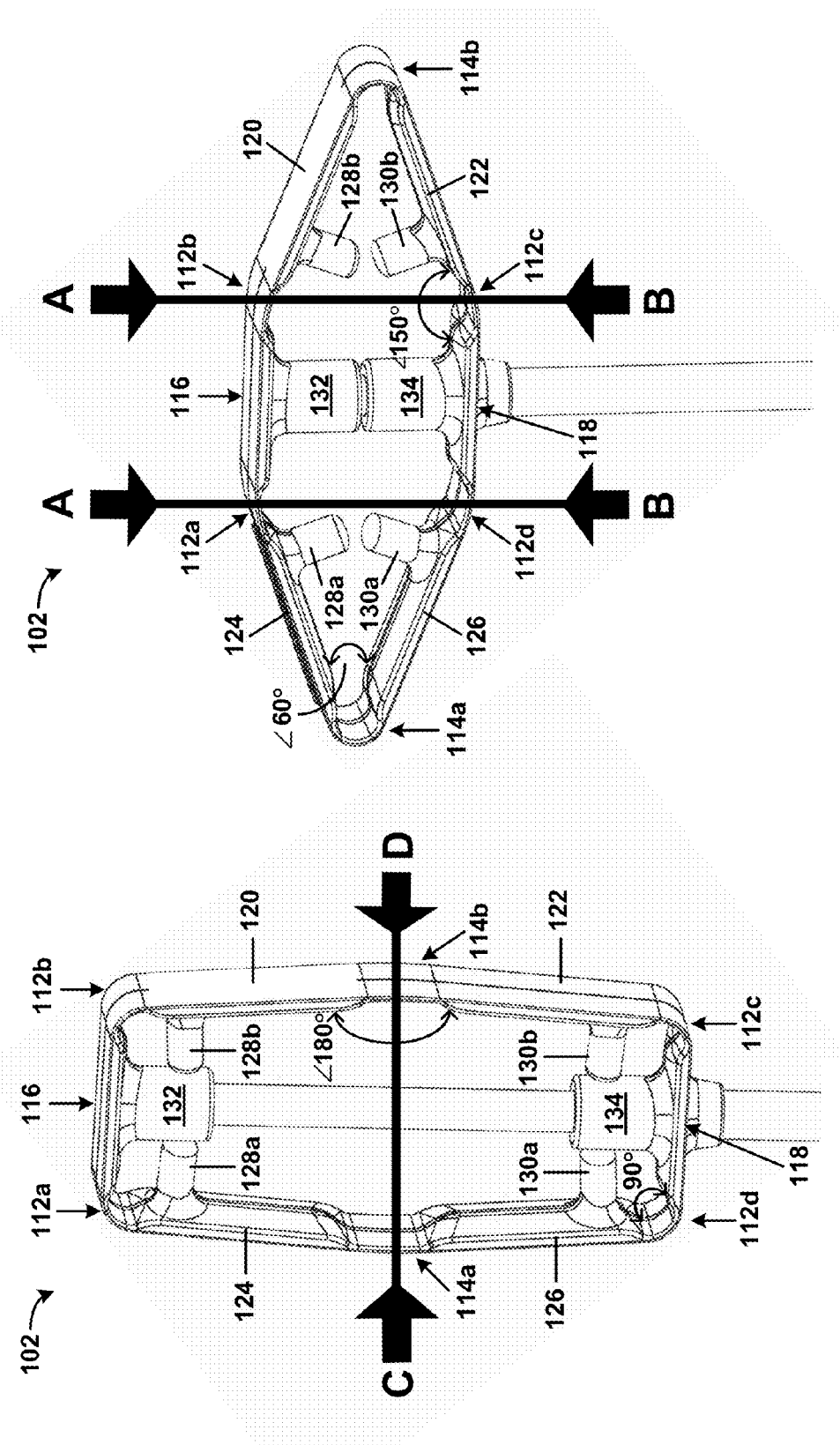

HANDLE FOR ACTUATING A DEVICE

FIELD

The present disclosure relates to a mechanical device, a handle for the mechanical device, and a method for cleaning or removing contamination from a medical camera. In examples, the present disclosure relates to a medical device for increasing visibility of a laparoscope lens during surgery.

BACKGROUND

During laparoscopic surgery, a distal laparoscope lens frequently becomes contaminated due to contact with blood or tissue, or may become foggy due to condensation. When the lens becomes contaminated or foggy, the lens provides a reduced visibility. This reduced visibility generally requires a surgeon to remove the laparoscope, clean the lens, soak the lens in warm saline in a thermos to prevent fogging when returned into a warm humid environment of an abdomen, and finally replacing the laparoscope into the abdomen. Often, when the laparoscope is replaced, the laparoscope lens may touch tissue in or at a distal end of a cannula requiring the cleaning procedure to be repeated. These activities are generally repeated several times during a surgery.

Repeated removal of the laparoscope for lens cleaning interrupts the surgical procedure, wasting valuable time in the operating room. These interruptions are a frustration to the surgeon(s), cause delay in the operation, and may complicate the operation as well. For example, after the laparoscope is reinserted into the abdomen (following a cleaning procedure), the laparoscope will need to be rotated and adjusted to return to a previous view, and a step in the procedure is generally restarted where the interruption occurred. Stopping and restarting the procedure can lead to mistakes. Also, a frequent source of offending contamination includes a severed blood vessel. In such an instance, at a time that this issue should be dealt with quickly, the surgeon may not be able to see well enough to stop the bleeding, and thus, the procedure may need to be interrupted while the bleeding continues in order to clean the laparoscope lens.

SUMMARY

In one example, a device is described that comprises a shaft that includes a rod, an element coupled to a distal tip of the rod, and a handle coupled to a proximal end of the rod. The distal tip of the rod may provide an internal structure for the element. Actuation of the handle into a first position may cause deployment of the element from the shaft and actuation of the handle into a second position may cause retraction of the element into the shaft.

In another example, a device is described that comprises a shaft that includes a rod, and a sponge coupled to a distal tip of the rod. The distal tip of the rod may extend to a distal end of the sponge, and the sponge may be in a compressed form within the shaft and in an expanded form deployed from the shaft. The shaft may be configured for insertion into a human body.

In still another example, a device is described that comprises a shaft that includes a rod, a sponge coupled to a distal end of the rod, and a handle coupled to a proximal end of the rod. Actuation of the handle into a first position may cause deployment of the sponge from the shaft and actuation of the handle into a second position may cause retraction of the sponge into the shaft. In addition, actuation of the handle into the first position may cause the handle to be configured in a substantially hexagonal shape, and actuation of the handle into the second position may cause the handle to be configured in a substantially rectangular shape.

In another example, a handle is described that comprises a top comprising a first end and a second end, a first top side coupled to the first end of the top via a first corner hinge, and a second top side coupled to the second end of the top via a second corner hinge. The handle further comprises a first bottom side coupled to the first top side via a first side hinge, a second bottom side coupled to the second top side via a second side hinge, and a bottom coupled to the first bottom side via a third corner hinge and coupled to the second bottom side via a fourth corner hinge.

In another example, a handle is described that comprises a top, a bottom, and a first side and a second side coupled to the top and the bottom via corner hinges. The first side and the second side include side hinges.

In yet another example, a handle for a laparoscopic lens internal cleaning device is described. The handle may be coupled to a proximal end of the device. Actuation of the handle into a first position may result in the handle being configured in a substantially hexagonal shape and may cause deployment of a sponge from the device. Actuation of the handle into a second position may result in the handle being configured in a substantially rectangular shape and may cause retraction of the sponge into the shaft.

In further examples, methods for operating a device, methods for introducing a cleaning device into a body, and methods for actuating a cleaning device are provided.

The foregoing summary is illustrative only and is not intended to be in any way limiting. In addition to the illustrative aspects, embodiments, and features described above, further aspects, embodiments, and features will become apparent by reference to the figures and the following detailed description.

BRIEF DESCRIPTION OF THE DRAWINGS

FIGS. 3E-3F illustrate example operation of a handle of the device in FIG. 1.

DETAILED DESCRIPTION

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Laparoscopy is a form of surgery in which instruments are introduced into a body wall (e.g., an abdominal cavity) through puncture orifices or incisions into the abdominal wall. The incisions may be generally small incisions (e.g., 0.5-1.5 cm). Laparoscopic procedures generally use a trocar that comprises a cannula or trocar sleeve (a hollow sheath or sleeve with a central lumen). The trocar can be used to penetrate the abdominal wall, and the cannula can be inserted into the abdominal cavity. The cannula remains in the body wall throughout the surgical procedure and instruments used during laparoscopic procedures may be introduced into the abdomen through the cannula. Trocars, including cannulae, are available in different sizes to accommodate various surgical needs.

An example instrument that may be introduced into the body wall through a cannula, for example, includes a laparoscope. A laparoscope includes a lens at a distal end that may be coupled to a camera to enable visualizing an interior of an abdominal cavity. A laparoscope may be used to inspect and diagnose a condition or to perform surgery.

In some instances, the camera lens of the laparoscope may become obscured during surgery. For example, during surgery, the camera lens may become contaminated due to contact with blood or tissue, or foggy due to condensation.

This disclosure may disclose, inter alia, devices, systems, and methods for cleaning or removing contamination from a lens of a medical camera, or for increasing visibility of a laparoscope lens during surgery. As an example, a device may be introduced into the abdomen through a cannula that includes a sponge that may be used to clean the lens. The cannula can be inserted through one of several trocar cannula already in place for a variety of minimally invasive instruments used during procedures. After inserting the cannula, the sponge on the device can be deployed by the surgeon to clean the lens, for example.

Figure 1A:
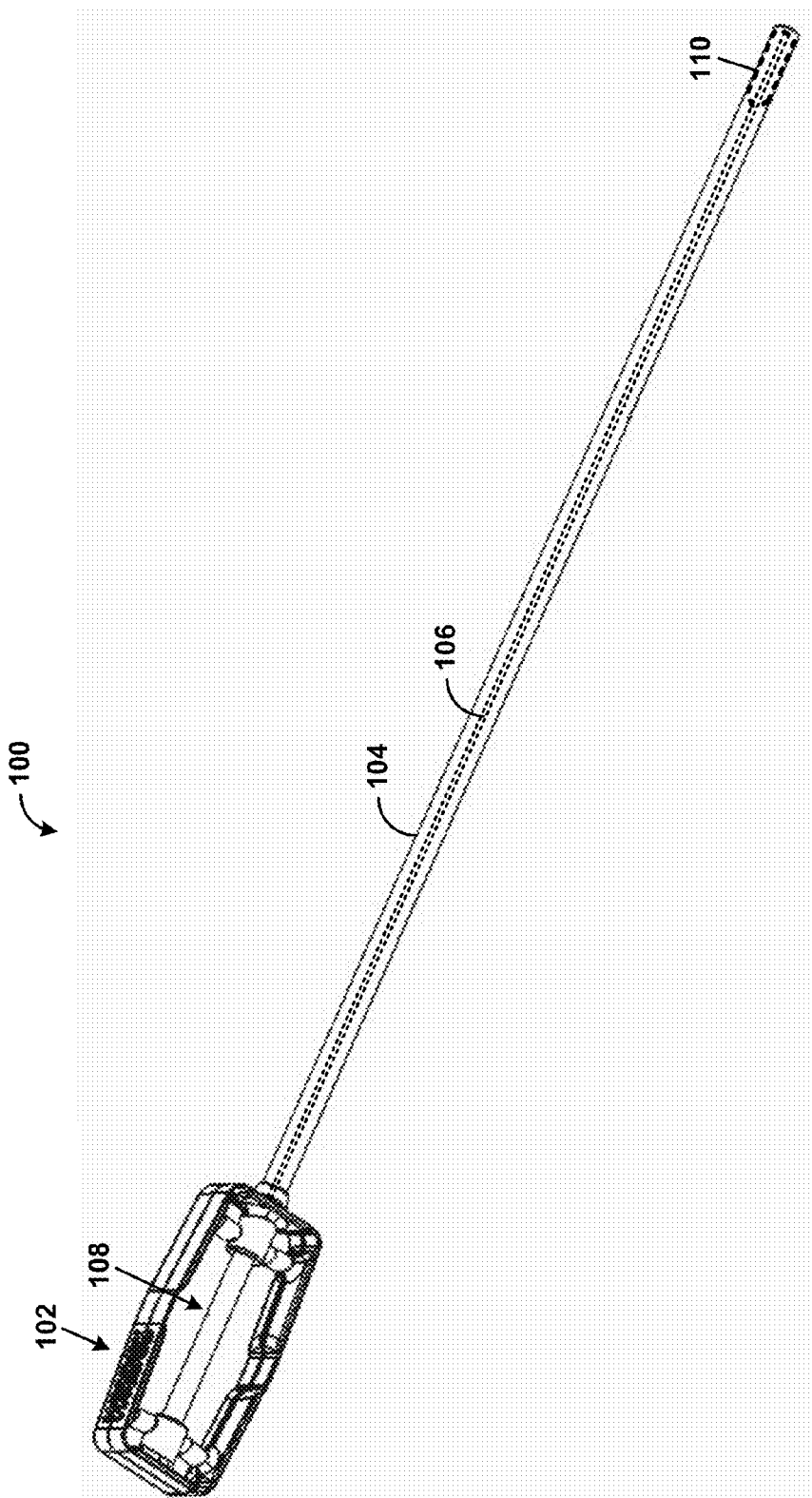
FIGS. 1A-1B illustrate an example device.
Figure 1B:
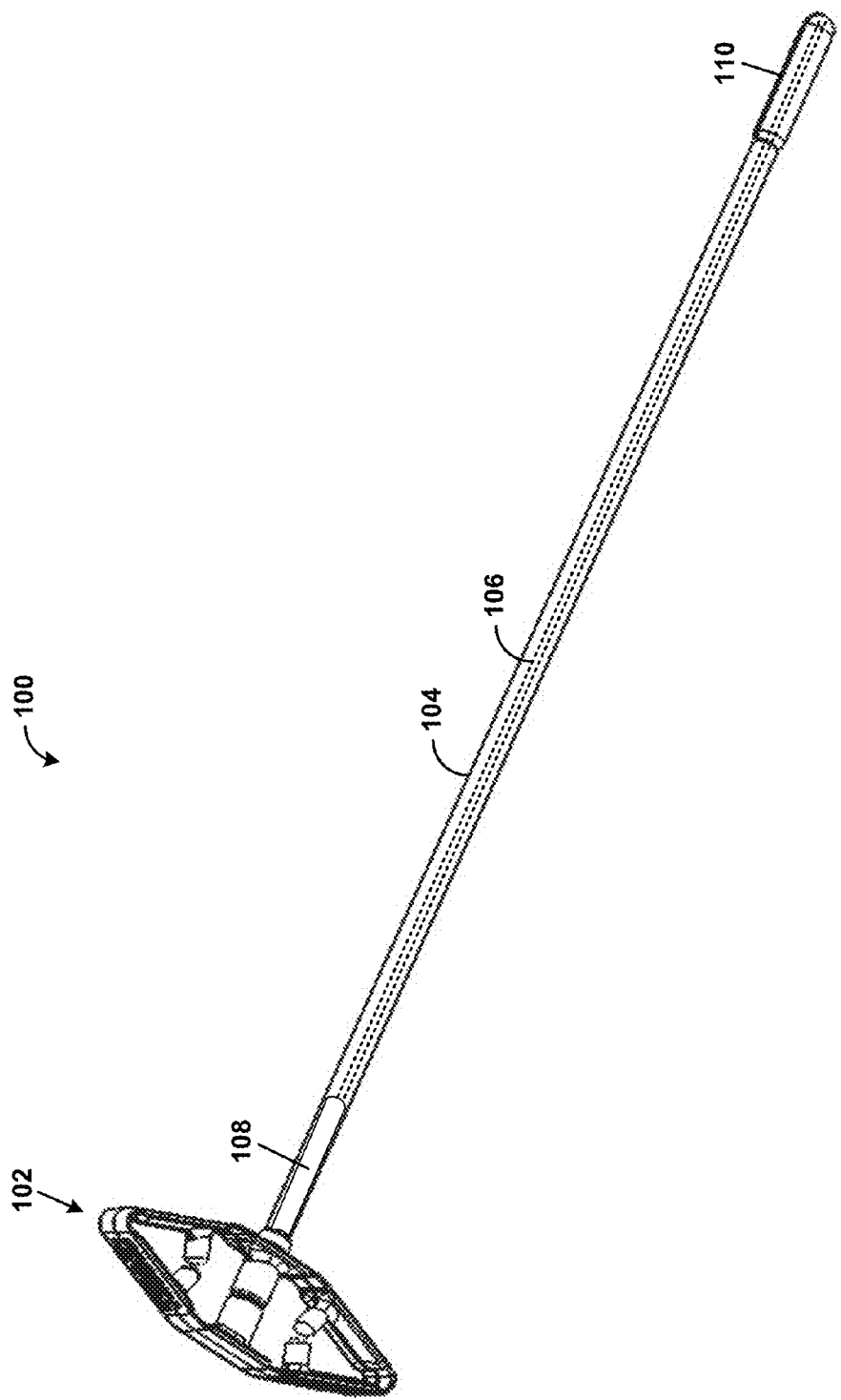

Referring now to the figures, FIGS. 1A-1B illustrate an example device 100. The device 100 includes a handle 102 coupled to a shaft 104. The shaft 104 includes a rod 106, and the shaft 104 may be a housing for the rod 106 such that the rod 106 is entirely within the shaft 104 in one configuration, for example. One end of the rod 106 may be coupled to the handle 102 via an actuation member 108, and the other end of the rod 106 may be coupled to a sponge 110. The rod 106 may extend to a distal end of the sponge 110 or may substantially extend to a distal end of the sponge 110, for example. In some examples, the actuation member 108 and the rod 106 may be the same element, and thus, one end of the rod 106 may be coupled to the handle 102 and the other end of the rod 106 may be coupled to a sponge 110.

The handle 102 may comprise a plastic material, and portions of the handle 102 may be flexible in some examples. The shaft 104 may comprise plastic, metal, glass, fiberglass or combinations of plastic, metal, glass and fiberglass, and may be of various lengths including about 4 inches to about 16 inches depending on an application of the device 100, for example. The shaft 104 and/or rod 106 may comprise materials such that the shaft 104 and/or rod 106 are flexible or rigid. The shaft 104 may be generally tubular, cylindrical, or other shape that is configured for insertion into a human body or a body cavity. The shaft 104 may be about 10 inches to about 16 inches long, depending on an application of the device 100. The shaft 104 may be hollow, such as a hollow tube or cannula. The rod 106/actuation member 108 may comprise similar materials as the shaft 104, and may be of similar sizes and shapes.

In one example, the rod 106 and the actuation member 108 may be the same component. For instance, the rod 106 may extend from a top of the handle 102 through an opening at a bottom of the handle 102 and into the shaft 104, and may be connected to the sponge 110. In this example, the actuation member 108 may be a proximal end of the rod 106.

The sponge 110 may comprise a porous material that may absorb fluid. In some examples, the sponge 110 may include a material comprising cellulose wood fibers, or foamed plastic polymers. The sponge 110 may include other synthetic materials, such as low-density polyether or polyester. The sponge 110 may also include open cell foam, closed cell foam, or hydrophilic and hydrophobic materials. The sponge 110 may be in a compressed form within the shaft 104, and thus, the sponge 110 may have a diameter larger than that of the shaft 104. The sponge 110 may thus expand upon being deployed from the shaft 104.

In some examples, the size of the sponge 110 relative to a size of the shaft 104 helps maintain deployment or retraction of the sponge 110. For instance, during retraction, the sponge 110 is compressed in the shaft 104 holding the sponge 110 in place. During deployment, the sponge 110 is expanded outside of the shaft 104 holding the sponge 110 in place. The sponge 110 may be of any length, and in examples, may be about 0.25 inches to about 2 inches in length. In some examples, a length of the sponge 110 may be about less than or equal to a length of exposed rod 106 in a deployed position.

FIG. 1A illustrates the device 100 in a retracted form, in which the handle 102 has not been actuated, or alternatively, has been actuated to cause the device to be in the retracted form. In the retracted form, the sponge 110 remains inside the shaft 104, as shown in FIG. 1A. In some examples, in retracted form the sponge 110 may remain fully inside the shaft 104 (as shown), and in other examples, the sponge 110 may remain at least substantially inside the shaft 104. In still another example, a cover (not shown) may be present at the distal end of the shaft 104 to provide an enclosed shaft 104 during the retracted form of the device 100.

FIG. 1B illustrates the device 100 in a deployed form, in which the handle 102 has been actuated in an actuation configuration. In the deployed form, the actuation member 108 pushes against the rod 106 (or the handle 102 pushes against the rod 106) causing the sponge 110 to be deployed out of the shaft 104. In an example in which the actuation member 108 and the rod 106 are the same element, actuation of the handle 102 causes the rod 106 to deploy. In some examples, in the deployed form the sponge 110 may be fully deployed from the shaft 104, and in other examples, a portion of the sponge 110 may be deployed.

An extent of deployment of the sponge 110 may be related to an amount of actuation of the handle 102. For example, in operation of the device 100, a top and bottom of the handle 102 may be squeezed or a top of the handle 102 may be pressed to cause the actuation member 108 to move the rod 106 in a distal direction forcing the sponge 110 out of the shaft 104. A length that the actuation member 108 moves may be the same as (or substantially equivalent) to a length that the rod 106 moves, which in turn, may be the same as (or substantially equivalent) to an amount of the sponge 110 that will be forced out of the shaft 104, for example.

As another example of operation of the device 100, sides of the handle 102 may be squeezed to cause a retraction of the sponge 110 into the shaft 104. In one example, a retraction of the sponge 110 may use a grip strength of a user, along with a mechanical advantage of the handle 102 to enable compression of the sponge 110 during retraction into the shaft 104. For instance, the sponge 110 may be of a size or have a diameter larger than a diameter of the shaft 110, such that the sponge 110 expands during deployment and the sponge 110 compresses during retraction.

In one example, the shaft 104 is hollow and the rod 106 may be positioned within the shaft 104. The rod 106 may move freely within the shaft 104 via actuation of the handle 102. When the device 100 is in a configuration as shown in FIG. 1A, with the handle 102 in an open position, the sponge 110 is retracted. No tension/force may be needed to be applied to the handle 102 to enable the device 100 to be in or remain in the configuration shown in FIG. 1A. The configuration of the device 100 may be considered a default position, for example. When the device 100 is in a configuration as shown in FIG. 1B, with the handle 102 in a closed position, the sponge 110 is deployed. In some examples, a tension or force may be applied to the handle 102 to force the rod 106 to hold in place for deployment of the sponge 110. In other examples, following deployment of the sponge 110 via actuation of the handle 102, no tension/force is needed to maintain deployment of the sponge 110. The handle 102 may lock in the closed position due to a mechanical locking structure (not shown), or may effectively lock in the closed position due to elasticity of material of the handle 102, for example. In addition, the sponge 110 may expand upon deployment thus providing a locking effect and holding the handle 102 and rod 106 in a deployed configuration since the sponge 110 may not retract back into the shaft 104 without an applied force, for example. Thus, in some examples, the sponge 110 in an expanded configuration may hold the deployed position, while the sponge 110 in a compressed configuration may hold the retracted position.

In other examples, the shaft 104 may include threads, and the rod 106 may include corresponding threads such that the rod 106 may move via actuation of the handle 102 causing the rod 106 to be driven along the threads similar to a screw mechanism. Upon deployment of the sponge 110, the threaded device may hold the rod 106 in a given position causing the sponge 110 to remain deployed, for example.

Figure 2B:
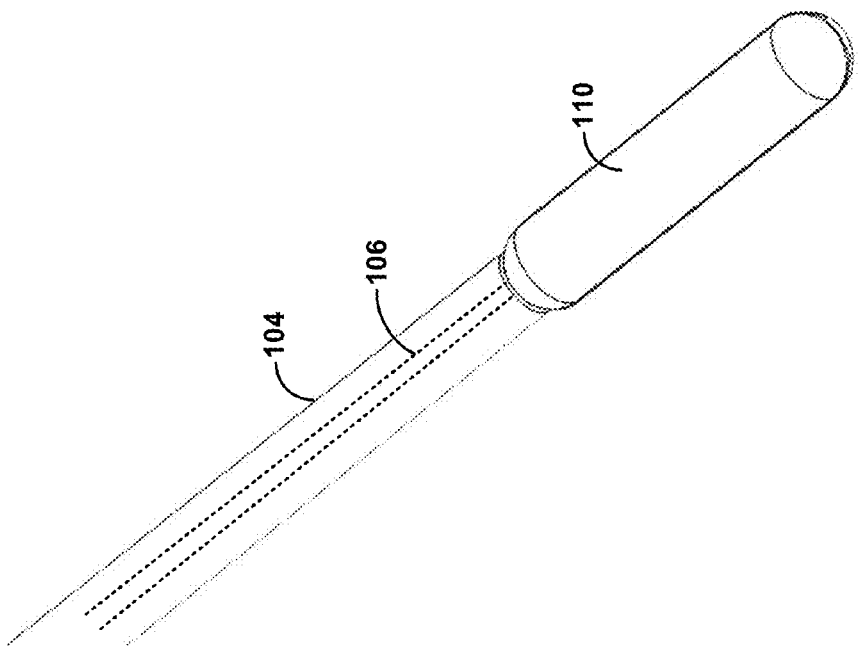
FIGS. 2A-2B illustrate a distal portion of the device in FIG. 1.
Figure 2A:
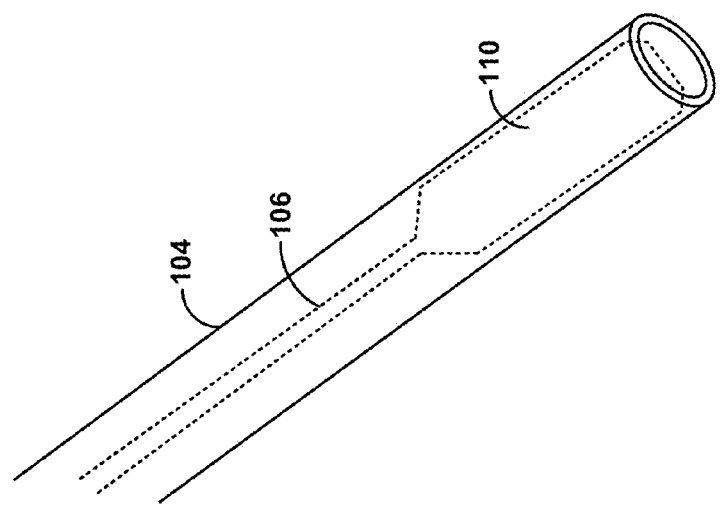

FIGS. 2A-2B illustrate a distal portion of the device in FIG. 1. FIG. 2A illustrates an example of the sponge 110 inside the shaft 104 when the sponge 110 is not deployed. In FIG. 2A, the sponge 110 may be compressed inside the shaft 104. FIG. 2B illustrates an example of the sponge 110 deployed. As shown in FIG. 2B, the sponge 110 expands upon deployment to have a larger surface area and a larger shape.

In some examples, the sponge 110 may be coupled to the rod 106 and may not be interchangeable. In other examples, the sponge 110 may be an interchangeable, disposable component, such that the sponge 110 may be used and disconnected from the rod 106 and replaced with a new sponge.

In addition, although FIGS. 2A-2B illustrate the sponge 110 coupled to the rod 106 at a distal end of the device 100, other elements may be coupled to the rod 106. For example, elements such as a gripper, a claw, scissors, a needle, a knife, a light, or any other elements generally used during medical surgery may be coupled to the rod 106. Thus, generally, any type of element, or combination of elements, that may be used during surgery and that can be retracted and deployed from the shaft 104 may be coupled to the rod 106.

Figures 3A, 3B:
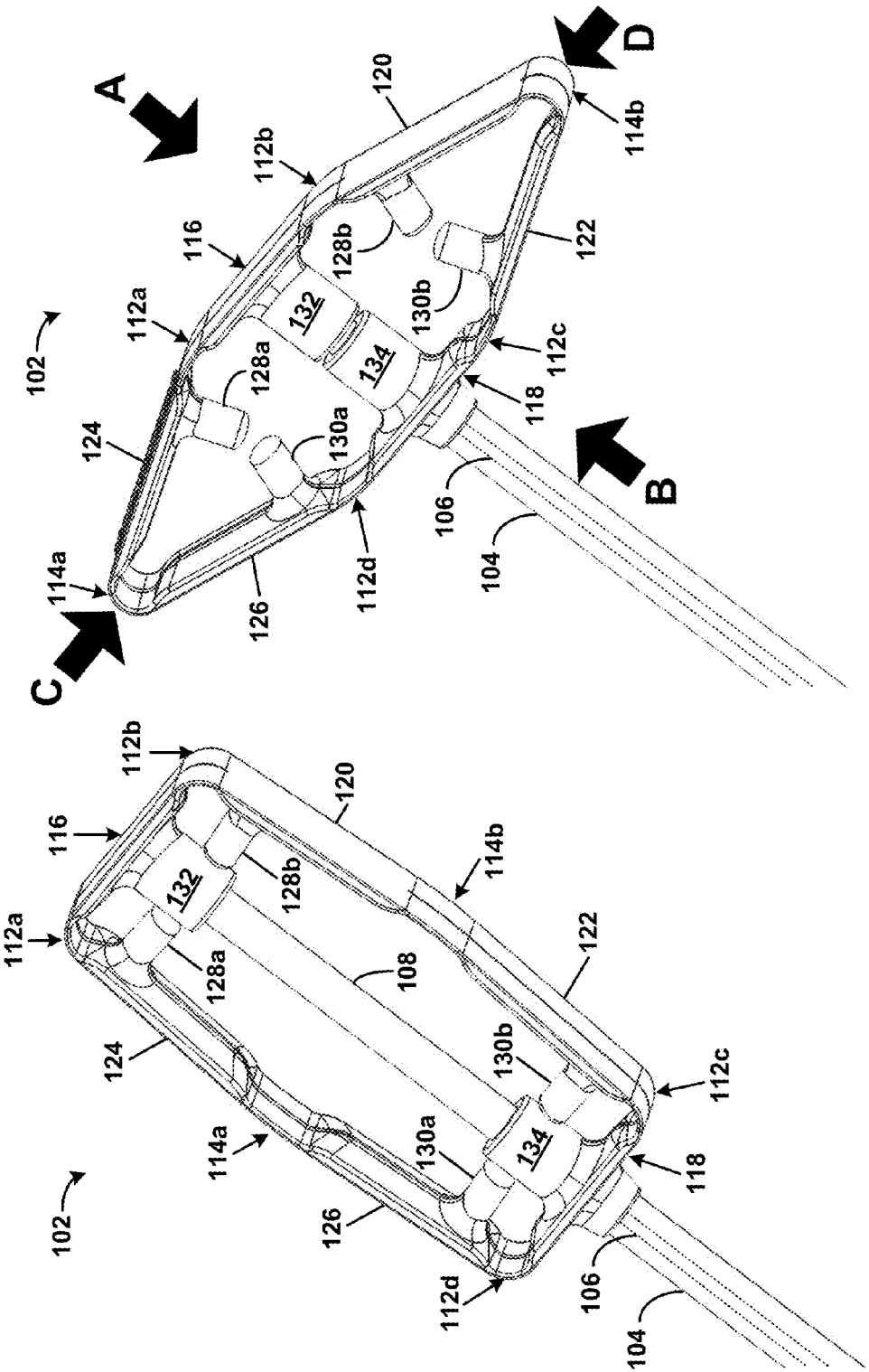
FIGS. 3A-3B illustrate a proximal portion of the device in FIG. 1.

FIGS. 3A-3B illustrate a proximal portion of the device 100 in FIG. 1 including the handle 102. In FIG. 3A, the handle 102 is in a position such that the sponge 110 is not deployed or is retracted (as shown in FIG. 1A). In FIG. 3B, the handle 102 is in a position such that the sponge 110 is deployed (as shown in FIG. 1B).

The handle 102 includes corner hinges 112*a-d* and side hinges 114*a-b* that coupled together a top 116, a bottom 118, and sides 120, 122, 124, and 126. Sides 120 and 124 may be top sides (e.g., opposing top sides), and sides 122 and 126 may be bottom sides (e.g., opposing bottom sides). In another example, the sides 120 and 122 may be considered a first side of the handle 102 that includes the side hinge 114*b* at a central position, and the sides 124 and 126 may be considered a second side of the handle 102 that includes the side hinge 114*a* at a central position. In other examples, the handle 102 may not include explicit hinges (e.g., hinges 112*a-d* and 114*a-b*), but rather, the material comprising the perimeter of the handle 102 including the top 116, the bottom 118, and the sides 120, 122, 124, and 126 may be of a flexible material that enables the handle 102 to bend or flex as shown in FIGS. 3A-3B.

The top 116 and the bottom 118 may be about the same length, and the sides 120, 122, 124, and 126 may be about the same length. In addition, the sides 120, 122, 124, and 126 may have a larger length than a length of the top 116 or a length of the bottom 118.

The handle 102 further includes top side stoppers 128*a-b*, bottom side stoppers 130*a-b*, and a top middle stopper 132 and a bottom middle stopper 134. Each of top sides 120 and 124 may include a top side stopper 128*a-b* on an inner surface of the top side 120 and 124. Similarly, each of the bottom sides 122 and 126 may include a bottom side stopper 130*a-b* on an inner surface of the bottom side 122 and 126.

In one example, the rod 106 is attached to a top of the handle 102 at the top middle stopper 132 (e.g., within a receiver hole of the top middle stopper 132), and the rod 106 passes through an opening of the bottom middle stopper 134. The shaft 104 may be fixed to the bottom 118 and/or to the bottom middle stopper 134.

The handle 102, and all components of the handle 102, may comprise one integral piece. Alternatively, components of the handle 102 may be coupled together using snap-tight connections, glue, welds, screws, etc.

Thus, the top 116, the bottom 118, the side 120, 122, 124, and 126, the corner hinges 112*a-d*, and the side hinges 114*a-b* may be one integral component, or may be manufactured from one piece of material, for example. Components of the handle 102 may comprise a flexible material, such as a plastic. For example, the corner hinges 112*a-d* and the side hinges 114*a-b* may be a plastic material that may bend under a force. In one example, the corner hinges 112*a-d* and the side hinges 114*a-b* may be or may include a "living hinge". For instance, the corner hinges 112*a-d* and the side hinges 114*a-b* enable the handle 102 to be compressed both in a lengthwise and a widthwise direction.

FIG. 3B illustrates an example of the handle 102 compressed in a lengthwise (longitudinal) direction. To do so, a user may squeeze the handle 102 by pressing the top 116 and the bottom 118 toward each other as shown by Arrows A-B. The handle 102 may be compressed lengthwise any amount and to an extent such that the top side stoppers 128*a-b* contact the bottom side stoppers 130*a-b*, and the top middle stopper 132 contacts the bottom middle stopper 134. In addition, or alternatively, the handle 102 may be compressed any amount and to an extent such that the top middle stopper 132 contacts the bottom middle stopper 134 (the top side stoppers 128*a-b* may not contact the bottom side stoppers 130*a-b* when fully compressed). When the handle 102 is compressed as shown by Arrows A-B, the actuation member 108 may be forced into the shaft 104 and push the rod 106 in a distal direction.

FIG. 3A illustrates an example of the handle 102 compressed in a widthwise (lateral) direction. To do so, a user may squeeze the handle 102 by pressing the side hinge 114a toward the side hinge 114b as shown by Arrows C-D in FIG. 3B. In addition, or alternatively, a user may press sides 120 and 122 toward sides 124 and 126. The handle 102 may be compressed widthwise any amount and to an extent such that the top side stoppers 128a-b contact the top middle stopper 132, and the bottom side stoppers 130a-b contact the bottom middle stopper 134. The actuation member 108 may be coupled to the top middle stopper 132 or the top 116, such that when the handle 102 is compressed as shown by Arrows C-D, the actuation member 108 is retracted from the shaft 104 and pulls the rod 106 in a proximal direction.

Figure 3C:
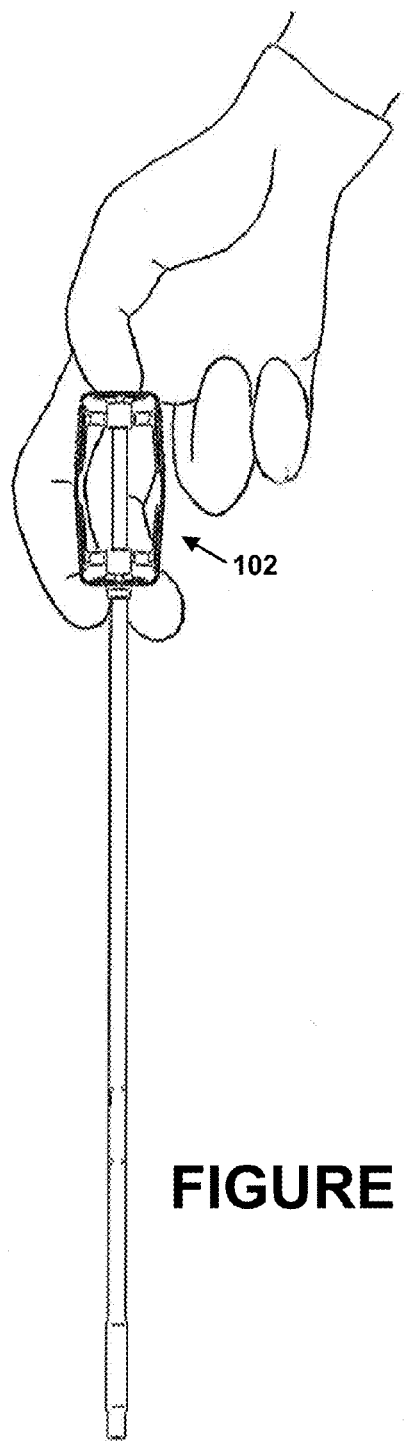
FIGS. 3C-3D illustrate conceptual example operation of the device in FIG. 1.
Figure 3D:
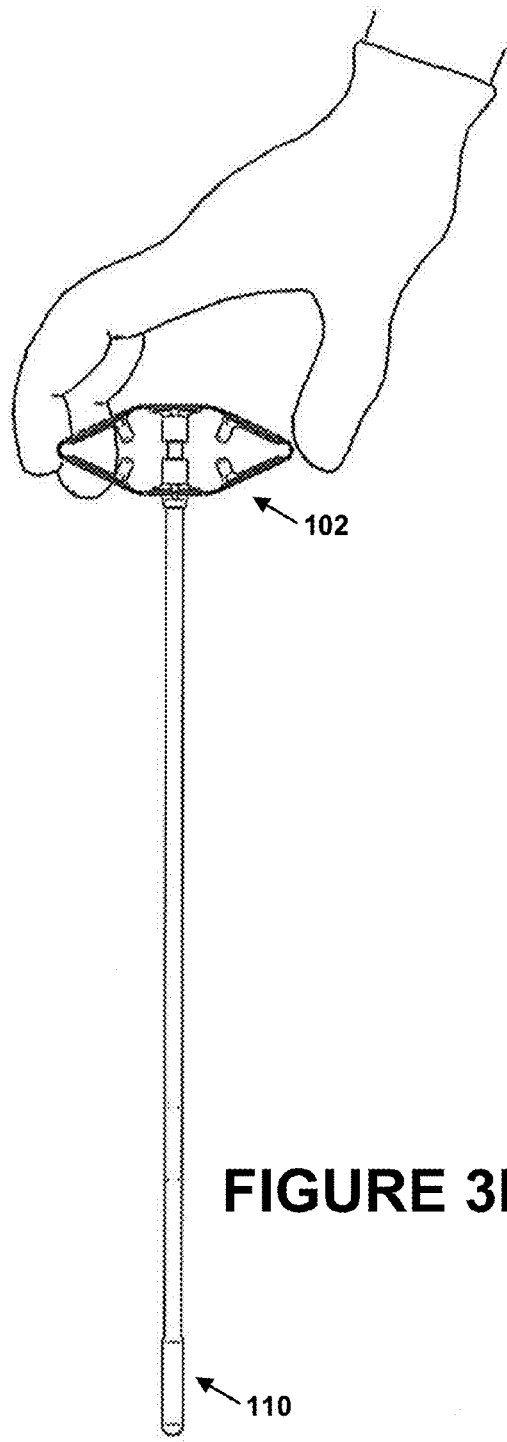

FIGS. 3C-D illustrate conceptual example operation of the handle 102 being compressed laterally and longitudinally. FIG. 3C illustrates a user compressing the handle 102 in a lateral manner to deploy the sponge 110. FIG. 3D illustrates a user compressing the handle 102 in a longitudinal manner to retract the sponge 110.

As shown in FIG. 3A, the handle 102 may be configured to be in a form of a rectangular shape. In other examples, the handle 102 may be a square, oval, or other shapes. As shown in FIG. 3B, the handle 102 may also be configured to be in a form of a hexagonal shape.

FIGS. 3E-3F illustrate example operation of the corner hinges 112a-d and side hinges 114a-b. The corner hinges 112a-d and the side hinges 114a-b generally connect portions of the handle 102 and allow an angle of rotation between the portions or allow portions of the handle 102 to rotate relative to each other about a fixed axis of rotation. As shown in FIG. 3E, side hinges 114a-b enable sides 120, 122, 124, and 126 to rotate about the line C-D depicted in FIG. 3E. In particular, a first top side 120 may rotate about the line C-D relative to a first bottom side 122 such that the first top side 120 and the first bottom side 122 are about 180° apart. Similarly, a second top side 124 may rotate about the line C-D relative to a second bottom side 126 such that the second top side 124 and the second bottom side 126 are about 180° apart. As shown in FIG. 3F, side hinges 114a-b further enable sides 120, 122, 124, and 126 to rotate toward each other. In particular, the first top side 120 may rotate about the line A-B relative to the first bottom side 122 such that the first top side 120 and the first bottom side 122 are about 60° apart. Similarly, the second top side 124 may rotate about the line A-B relative to the second bottom side 126 such that the second top side 124 and the second bottom side 126 are about 60° apart.

In addition, as shown in FIG. 3F, corner hinges 112a-d enable the sides 120, 122, 124, and 126 to rotate about an axis relative to the top 116 and the bottom 118. In particular, the first top side 120 may rotate about the axis relative to the top 116 such that the first top side 120 and the top 116 are about 150° apart. Similarly, the second top side 124 may rotate about the axis relative to the top 116 such that the second top side 124 and the top 116 are about 150° apart. In addition, the first bottom side 122 may rotate about the axis relative to the bottom 118 such that the first bottom side 122 and the bottom 118 are about 150° apart. Similarly, the second bottom side 126 may rotate about the axis relative to the bottom 118 such that the second bottom side 126 and the bottom 118 are about 150° apart.

As shown in FIG. 3E, corner hinges 112a-d further enable the sides 120, 122, 124, and 126 to rotate toward the top 116 and the bottom 118. In particular, the first top side 120 may rotate about the axis relative to the top 116 such that the first top side 120 and the top 116 are about 90° apart. Similarly, the second top side 124 may rotate about the axis relative to the top 116 such that the second top side 124 and the top 116 are about 90° apart. In addition, the first bottom side 122 may rotate about the axis relative to the bottom 118 such that the first bottom side 122 and the bottom 118 are about 90° apart. Similarly, the second bottom side 126 may rotate about the axis relative to the bottom 118 such that the second bottom side 126 and the bottom 118 are about 90° apart.

Thus, the lines A-B and C-D in FIGS. 3E-F depict a path that the side hinges 114a-b and corner hinges 112a-d travel through when flexing. The sides 120, 122, 124, and 126 rotate about an axis that is located at each hinge and extends in the Z direction with the lines A-B and C-D defining X and Y directions, for example. An amount of rotation allowed or enabled by the corner hinges 112a-d and the side hinges 114a-b may be limited due to contact of the top side stoppers 128a-b with the top middle stopper 132 and the bottom side stoppers 130a-b with the bottom middle stopper 134 in one example (shown in FIG. 3E), or due to contact of the top side stoppers 128a-b with the bottom side stoppers 130a-b and contact of the top middle stopper 132 with the bottom middle stopper 134 in another example (shown in FIG. 3F). In some examples, the side hinges 114a-b may have a greater amount of possible rotation than the corner hinges 112a-d. The side hinges 114a-b may allow rotation of components of the handle 102 in a range of about 45° to about 180°, and the corner hinges 112a-d may allow rotation of components of the handle 102 in a range of about 90° to about 180°, for example.

In some examples, the top 116, the first top side 120, the second top side 124, the first bottom side 122, the second bottom side 126, and the bottom 118 are configured to be a substantially rectangular shape, as shown in FIG. 3E. The substantially rectangular shape may result with the side hinges 114a-b configured to be at an angle of about 180° and each of the corner hinges 112a-d configured to be at an angle of about 90°. In other examples, the top 116, the first top side 120, the second top side 124, the first bottom side 122, the second bottom side 126, and the bottom 118 are configured to be a substantially hexagonal shape. The substantially hexagonal shape may result with the side hinges 114a-b configured to be at an angle of about 60° and each of the corner hinges 112a-d configured to be at an angle of about 150°. The handle 102 may be considered to be a substantially hexagonal shape with six vertices defined at positions of the side hinges 114a-b and the corner hinges 112a-d. The hexagonal shape of the handle 102 may further be considered an oval shape or substantially oval shape in some examples.

The handle 102 may be used for a variety of applications. As shown in FIGS. 3C-3D, the handle 102 may be used to deploy and retract a sponge. However, the handle 102 may be used for other applications as well to cause a rod to be pushed or pulled. This mechanical motion created by squeezing the handle 102 in either direction may have applications including opening and closing jaws for grasping or cutting, or articulating a distal tip, for example.

Figure 4A:
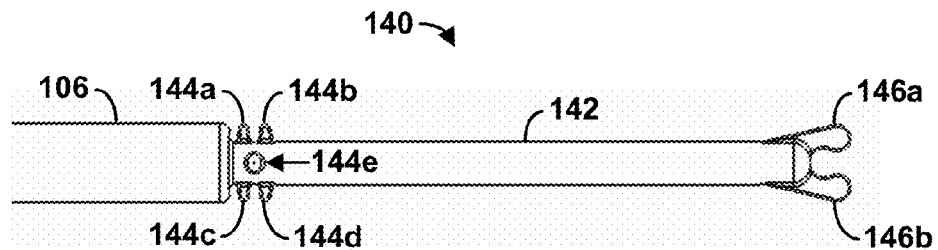
FIGS. 4A-4D illustrate example configurations for a sponge for devices described herein.

FIGS. 4A-4D illustrate example configurations for a sponge for devices described herein (such as for sponge 110 in FIG. 1B). FIG. 4A illustrates an example of a distal end 140 of the rod 106. The distal end 140 of the rod 106 includes a tip 142 with protuberances 144a-e and protuberances 146a-b. The tip 142 may have a smaller diameter than a remaining portion of the rod 106, for example.

The protuberances 144a-e and 146a-b may function as attachment points for sponge material or sponge element. In one example, the protuberances 144a-e and 146a-b are used to weld a sponge to the tip 142 during manufacturing. A sponge may be welded to the tip 142 of the rod 106 at both ends using protuberances 144*a-e* and protuberances 146*a-b*. The sponge material may be assembled to the rod 106 under tension so that the sponge material does not fold back on itself during retraction, which may allow the sponge material to have a larger diameter than the shaft 104, for example.

Figure 4B:
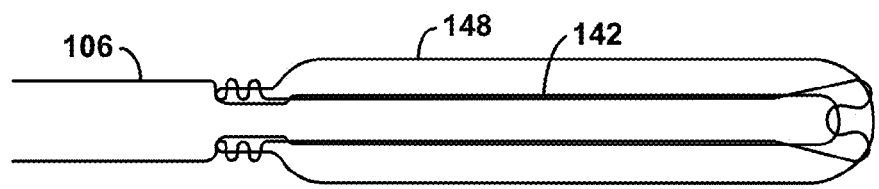

FIG. 4B illustrates an example of a sponge material 148 coupled to the tip 142 of the rod 106. The sponge material 148 may take the form of several different configurations. In one example, the sponge material 148 may include a compressible sponge in the shaft 104, and when deployed, the sponge material 148 may expand into a number of geometrical shapes (e.g., cylindrical or spherical). As shown in FIG. 4B, the rod 106 via the tip 142 extends to a distal end of the sponge material 148. In some examples, the tip 142 provides an internal structure to the sponge material 148. The tip 142 may enable the sponge material 148 to be rigid.

As another example, the tip 142 may be provided at an angle with respect to the rod 106 such that the tip 142 (and the sponge material 148) may bend away or toward the rod 106. The tip 142 may bend away or toward the rod 106 upon application of a force, for example.

Figure 4C:
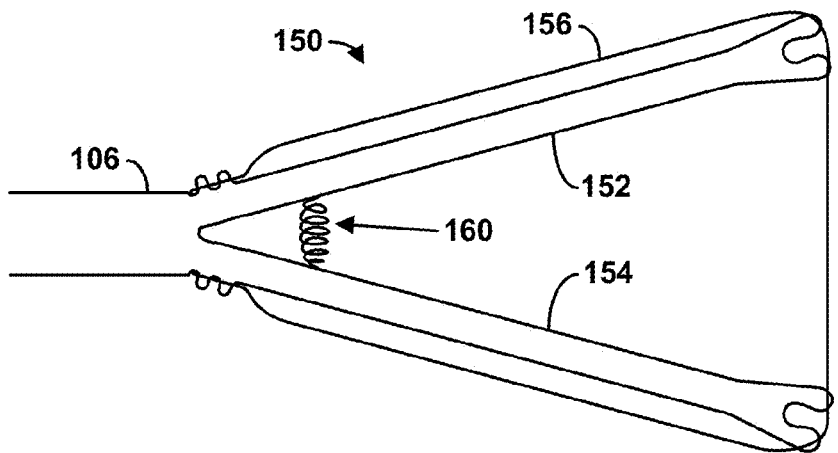

FIG. 4C is an alternate example of a distal end 150 of the rod 106. The distal end 150 may include two tips 152 and 154, and sponge material 156 may cover both tips 152 and 154. In this example, the distal end 150 includes multiple elements in a "Y" shape such that sponge material is provided around arms of the "Y" shape. The tips 152 and 154 may compress and bend at a junction of the tips 152 and 154. Upon deployment, the tips 152 and 154 may expand into the "Y" position due to a spring element 160 between the tips 152 and 154. In some examples, using the spring element 160 provides the tips 152 and 154 at various angles.

Figure 4D:
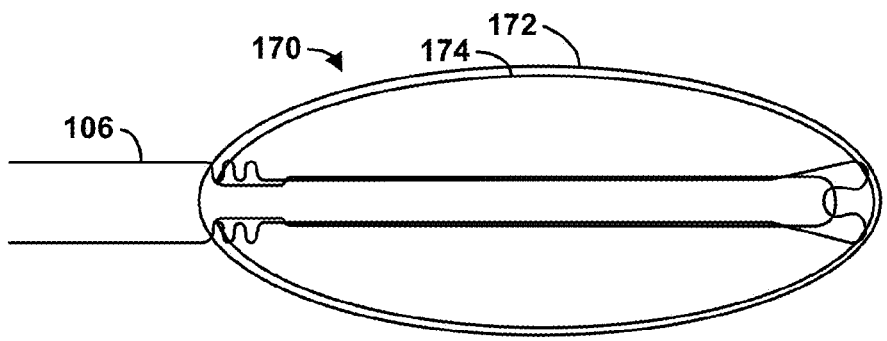

FIG. 4D is still another alternate example of a distal end 170 of the rod 106. In this example, sponge material 172 may be coupled to the distal end 170 of the rod 106. The sponge material 172 may cover a structure 174, which may be filled with air, saline, or a surfactant upon deployment of the device. The structure 174 may be a balloon-type structure comprising a flexible material. The structure 174 may create a firm surface upon which the sponge material 172 is present.

In some examples, using any of the configurations of a sponge device shown in FIGS. 4A-4D, sponge material may be of various sizes and shapes, and may include a triangle, square, or oval shape, and may be large enough to wipe about a 10 mm laparoscopic lens. Other examples and configurations are possible as well.

In some examples, using any of the configurations of a sponge device shown in FIGS. 4A-4D, a surfactant may be added to the sponge material to wet a sponge tip prior to use. An example solution may include Poloxamer 188. The sponge material may thus be pre-loaded with a fluid, such that after deployment, the sponge is moist.

Figure 5A:
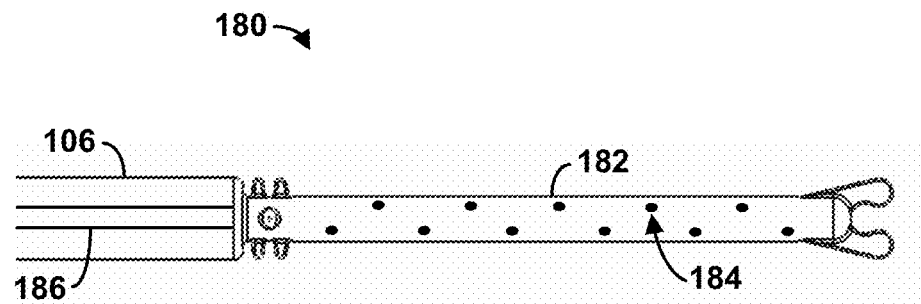
FIGS. 5A-5B illustrate additional example configurations for a sponge for devices described herein.
Figure 5B:
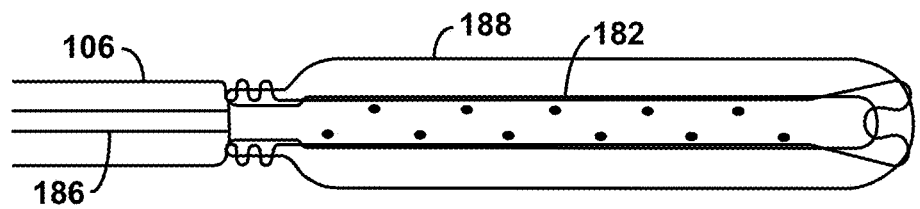

FIGS. 5A-5B illustrate additional example configurations for a sponge for devices described herein (such as for sponge 110 in FIG. 1B). FIG. 5A illustrates an example of a distal end 180 of the rod 106. The distal end 180 of the rod 106 includes a tip 182 with holes, such as hole 184. The rod 106 may include a fluid which can be pumped through the holes 184. In one example, the rod 106 may include a syringe 186.

FIG. 5B illustrates a sponge material 188 coupled to the tip 182. The syringe 186 may be filled with saline, and may be used to fill a hollow center of the sponge material 188 with saline. In some examples, this may distend a surface of the sponge material 188 to present a convex, flexible surface on which the lens may be wiped. Additionally, the sponge material 188 may "weep" as the saline slowly seeps through, which provides a cleaning action for the sponge material 188 and may prevent scratching of the lens.

Thus, using the example sponge configuration in FIGS. 5A-5B, saline or a surfactant fluid may be injected into the sponge material 188 to moisten the sponge material 188. As another example, holes may be present only in a half or one side of the tip 182 such that one side of the sponge material 188 may be moistened. Using this example, a surgeon may clean the lens with a moist side of the sponge material 188 and then rotate the sponge material 188 to present a dry side for a final cleaning.

Figure 6A:
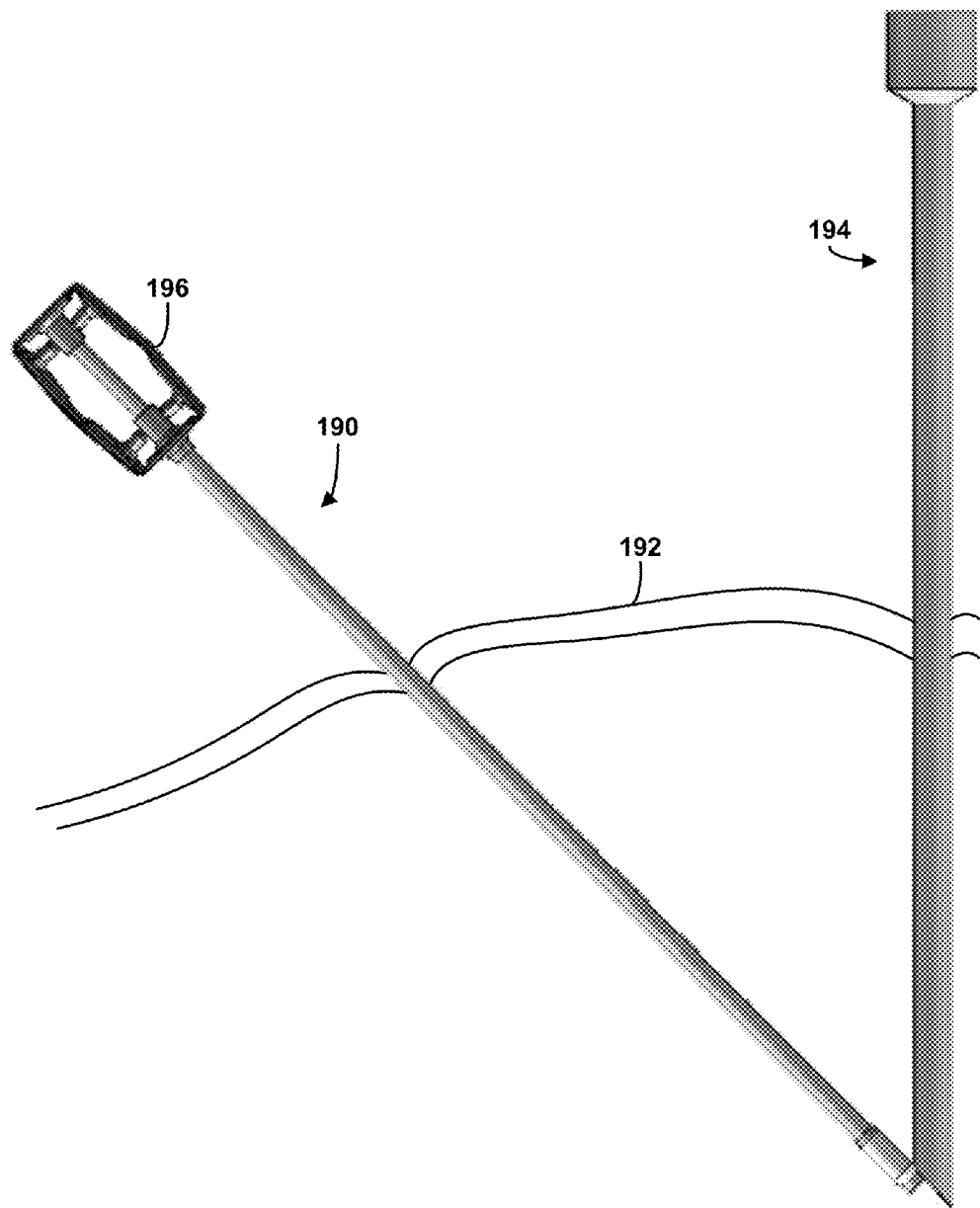
FIGS. 6A-6B illustrate an example operation of a laparoscopic lens internal cleaning system (LLICS).
Figure 6B:
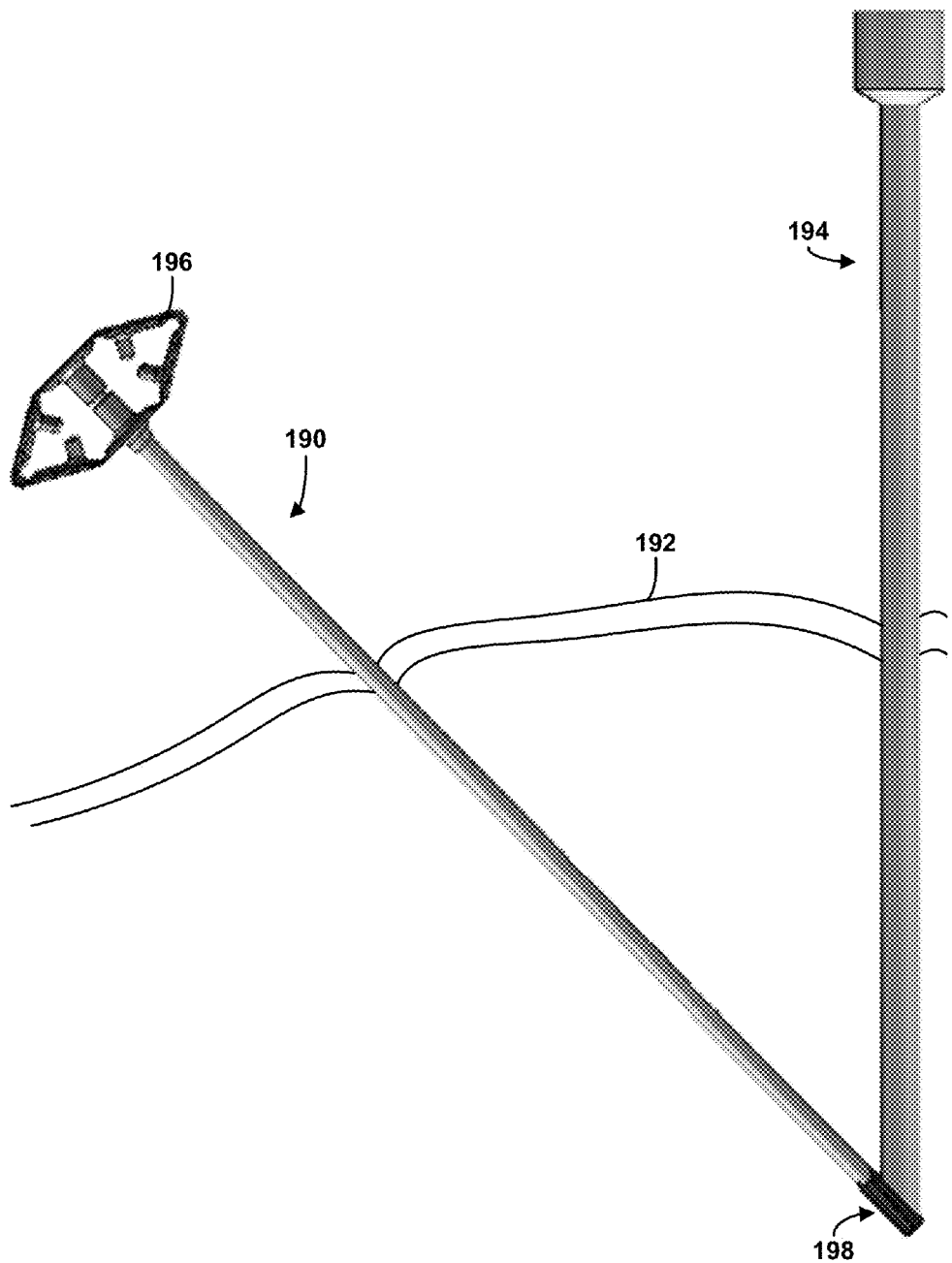

FIGS. 6A-6B illustrate an example operation of a laparoscopic lens internal cleaning system (LLICS) 190. The LLICS 190 may be similar to or the same as the device 100 in FIGS. 1A-1B. The LLICS 190 is shown inserted into a body cavity through a layer 192 of a body. The LLICS 190 may be inserted through one of several trocar cannulae in place for a variety of minimally invasive instruments used during procedures, such as micro-dissection scissors, suction, irrigation, retractors, graspers, ultrasonic or electrosurgical devices, etc. The LLICS 190 may be configured so as to fit through about a 5 mm laparoscopic access cannula, for example. Also, a device 194 is inserted into the body cavity. The device 194 may be or include a laparoscope lens, for example. In FIG. 6A, the LLICS 190 is shown with a handle 196 is an open position, such that no sponge is deployed.

FIG. 6B illustrates the LLICS 190 with the handle 196 in a closed position in which a sponge 198 is deployed at a distal end of the LLICS 190. The sponge 198 may be used to clean a lens of the device 194, for example. In operation of the LLICS 190, when a user presses a top of the handle 196, or squeezes the hexagonal from the top side, a sponge 198 extends out of the LLICS 190 at a distal end into a deployed position. When a user squeezes an outside of the handle 196, the sponge 198 retracts into the cannula with a mechanical advantage. The retraction motion uses grip strength, along with a mechanical advantage which helps compression of an oversized sponge during retraction, for example.

Thus, in an example use, a surgeon may retract the sponge 198 by squeezing the handle 196, insert the LLICS device 190 through an existing access cannula, and activate a deployment mechanism by pressing or squeezing the handle 196 from the top. This will drive the sponge 198 out the distal end of the device 190. The sponge 198 has a larger diameter than a cannula of the device 190, and is compressed when retracted. The sponge 198 can be used to clean the lens, retracted, and removed through the trocar access cannula. To remove, the surgeon may pull the push rod back by squeezing the handle in an opposite manner, and the sponge returns to an original position in the LLICS 190 for removal through the access cannula.

Thus, the handle 196 may be configured to be actuated into a first position by squeezing the handle 196 with the handle 196 oriented in a first direction to cause deployment of the sponge 198 from the shaft, and the handle 196 may be configured to be actuated into a second position by squeezing the handle 196 with the handle 196 oriented in a second direction to cause retraction of the sponge 198 into the shaft. The first direction may be perpendicular to the second direction. Actuation of the handle 196 into the first position may cause the handle 196 to be configured in a substantially hexagonal shape, and actuation of the handle 196 into the second position may cause the handle 196 to be configured in a substantially rectangular shape.

The device 190 can be used more than once, and may also be disposable. A rod/shaft of the device 190 may comprise a metal cannula and a plastic push rod that has fiberglass added for additional strength, for example. Thus, the device 190 may be used for other functions during a surgical procedure as well, such as to move/push (retract) objects or for soft tissue dissection.

Figure 7:
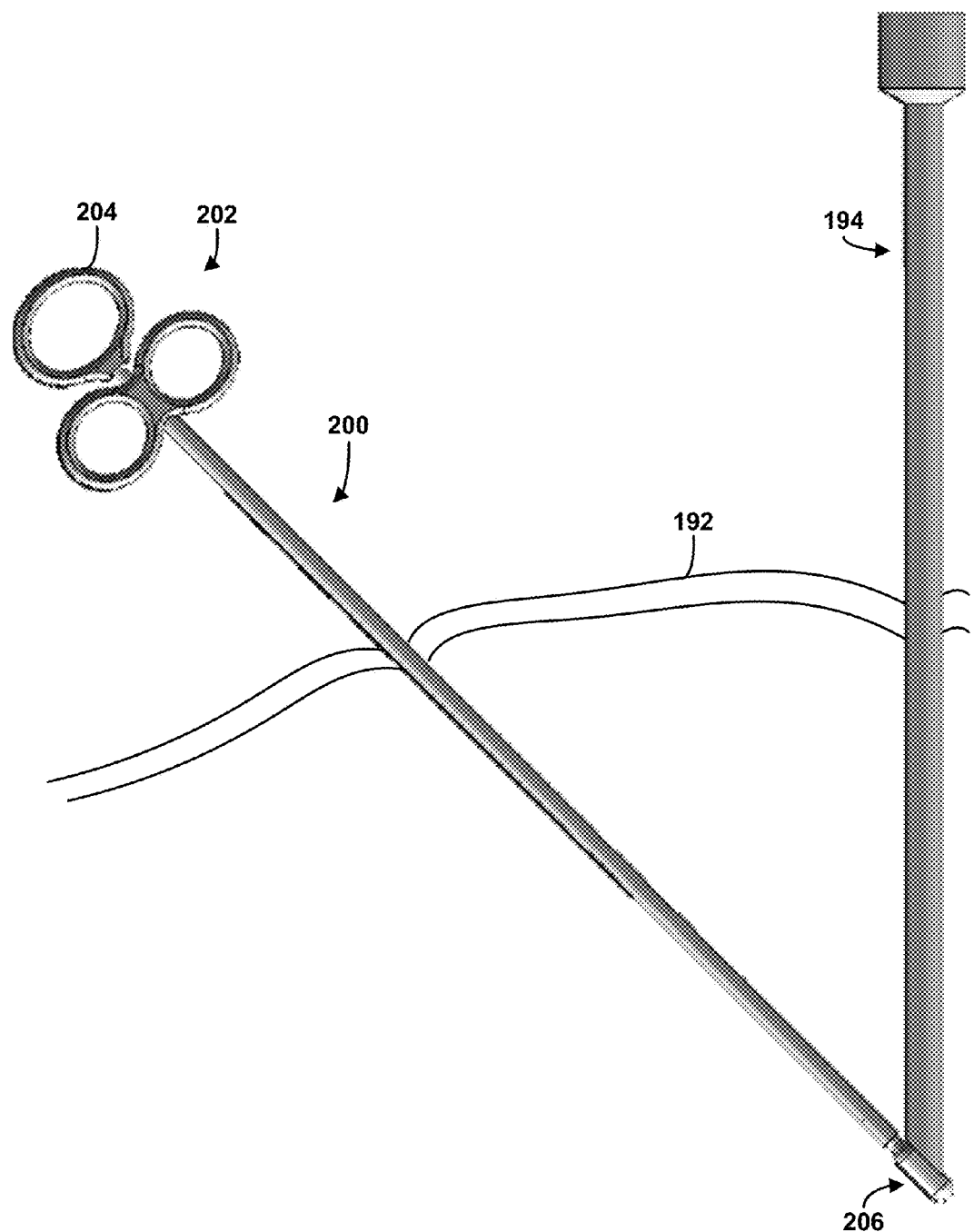
FIG. 7 illustrates an example operation of another laparoscopic lens internal cleaning system (LLICS).

FIG. 7 illustrates an example operation of another laparoscopic lens internal cleaning system (LLICS) 200. The LLICS 200 may be similar to the LLICS 190 shown in FIGS. 6A-6B. However, the LLICS 200 includes a handle 202 that has a different configuration. As shown, the handle 202 may include a syringe type handle with three holes for a surgeon's thumb, and first and middle fingers. A top component 204 may be pushed and pulled to deploy and retract a sponge 206.

Example configurations of devices described herein were tested using a computer-based endoscope test device called EndoBench™, made by Lighthouse Imaging Corporation of Portland, Me. Testing provided quantitative data of cleaning results of devices, such as device 100 in FIGS. 1A-1B, compared to other cleaning procedures used in surgery.

Examples tests were performed to quantify cleaning results using the device 100 to clean a lens of a scope. The lens of a scope (e.g., endoscope) was contaminated with various material, and the device 100 was used to clean the lens. Testing was performed to determine the Modulus Transfer Function (MTF), which is the optical parameter for clarity, of the lens after cleaning. The EndoBench™ may measure the MTF in five locations within an endoscope field of view; center, upper quadrant, right quadrant, lower quadrant, and left quadrant. An average of all five data points can be reported and a standard deviation can be calculated and reported. Results of testing are shown below in Table 1.

Initially, proximal and distal lenses of the scope were cleaned with wipes and denatured alcohol. The EndoBench MTF test was performed to determine a default measurement for a clean lens (92.7), and results are shown in Table 1 as line 1. Baseline (Test code #1). Following, the endoscope distal lens was contaminated with bovine blood. The EndoBench MTF test was performed to determine the MTF (8.2) of the contaminated lens, and results are shown in Table 1 as line 2. Blood (Test code #2). A Poloxamer 188 solution (10% solution by weight) was applied to a sponge of the device 100, the sponge was retracted for simulation of insertion into a body cavity, redeployed, and used to clean the contaminated lens. The sponge was 6.5 mm wide and 35 mm long, and comprised two layers of 2.75 mm thick polyurethane foam. Following, the EndoBench MTF test was performed to determine MTF of the cleaned lens (90.0), and results are shown in Table 1 as line 3. LLICS (Test code #3). Thus, after cleaning using the device 100, the lens optical clarity was approximately returned to the default clean state. The MTF measurements of the default clean state (92.7) and the LLICS clean state (90.0) are substantially the same.

As a second test, the endoscope distal lens was contaminated with bacon fat, and the EndoBench MTF test was performed to determine the MTF (23.2) of the contaminated lens, and results are shown below in Table 1 as line 4. Fat (Test code #4). A Poloxamer 188 solution was applied to a sponge of the device 100, the sponge was retracted for simulation of insertion into a body cavity, redeployed, and used to clean the contaminated lens. Following, the EndoBench MTF test was performed to determine MTF of the cleaned lens (89.3), and results are shown below in Table 1 as 5. LLICS (Test code #5). Again, here the cleaned lens measurement (89.3) is substantially the same as the default clean state (92.7).

Following, the lens was cleaned again by hand using denatured alcohol and wipes, and the EndoBench MTF test was performed to determine the MTF as a new baseline (92.1), and results are shown in Table 1 as line 6. Baseline (Test code #6). The lens was again contaminated with bovine blood and the EndoBench MTF test was performed to determine MTF (19.2) of the contaminated lens, and results are shown below in Table 1 as line 7. Blood (Test code #7). The lens was then cleaned using standard procedures including using a Medline sponge after soaking with a Medline anti-fog solution and wiping the lens by hand with the sponge, and the EndoBench MTF test was performed to determine MTF (89.8), and results are shown below in Table 1 as line 8. FRED (Test code #8). Cleaning using a sponge by hand simulates standard cleaning procedures as used during surgery in which a surgeon removes the scope from the body cavity, and the lens is cleaned by hand using a sponge and anti-fog solution (which is used so that upon reinsertion of the lens into the body cavity, the lens surface will not become foggy due to temperature changes of ambient environment versus internal body cavity). Cleaning using standard procedures produced an MTF (89.8) and demonstrated that the lens was approximately returned to the baseline MTF (92.1). In addition, the MTF for cleaning blood using standard procedures (89.8) was substantially the same as the MTF for cleaning blood using the device 100 (90.0), which demonstrates in this example, that the device 100 may be as effective or better at cleaning the lens. Further, the standard deviation calculated when cleaning blood from the lens using the device 100 (1.1) was better than that calculated when cleaning blood using standard procedures (2.7).

Following, the lens was contaminated with bacon fat, and the EndoBench MTF test was performed to determine MTF (15.4) of the contaminated lens, and results are shown below in Table 1 as line 9. Fat (Test code #9). The lens was then cleaned using standards procedures including using a Medline sponge after soaking with a Medline anti-fog solution, and the EndoBench MTF test was performed to determine MTF (91), and results are shown below in Table 1 as line 10. FRED (Test code #10). The MTF for cleaning fat using standard procedures (91) was substantially the same as the MTF for cleaning fat using the device 100 (89.3), which demonstrates in this example, that the device 100 may be as effective or better at cleaning the lens. Further, the standard deviation calculated when cleaning fat using the device 100 (1.3) was better than that calculated when cleaning fat using standard procedures (1.4).

TABLE 1

|  | MTF Avg. | Std. Dev. | % Decrease | Result |
| --- | --- | --- | --- | --- |
| 1. Baseline | 92.7 | 0.5 | — | Pass |
| 2. Blood | 8.2 | 1.5 | 91% | Pass |
| 3. LLICS | 90.0 | 1.1 | 3% | Pass |
| 4. Fat | 23.2 | 23.3 | 75% | Pass |
| 5. LLICS | 89.3 | 1.3 | 4% | Pass |
| 6. Baseline | 92.1 | 0.9 | — | Pass |
| 7. Blood | 19.2 | 10.2 | 79% | Pass |
| 8. FRED | 89.8 | 2.7 | 2% | Pass |
| 9. Fat | 15.4 | 8.1 | 83% | Pass |
| 10. FRED | 91 | 1.4 | 1% | Pass |

In this example, the denatured alcohol cleaned lens average MTF measurement can be taken as a baseline for comparison. For contamination, the contaminated lens was greater than a 50% reduction in average MTF from baseline. For a cleaned lens, the lens was less than a 5% reduction in average MTF from baseline, and a standard deviation was less than 3.0 for clean lens measurements. Standard deviation for contaminated lens measurements can be disregarded.

In example experiments, the average MTF for contaminated lenses was greater than a 50% reduction, which was determined to be successful for contaminating the lens. The average MTF decreased for all cleaned lenses, both with the device 100 and the control cleaning method, being less than 5% indicated that all cleanings passed example acceptance criteria. The standard deviation for all cleaned lenses was less than 3.0 indicating that all lenses were cleaned successfully in all areas of the lenses. The example experiments quantitatively demonstrate that the device 100 may perform substantially similar to current methods for cleaning lenses.

Example devices described herein may be used for cleaning a lens of a scope inside a patient during a surgical procedure. The lens may be attached to a distal end of an endoscope, such as a laparoscope, flexible endoscope, arthroscope, or gastroscope. A method for cleaning a lens of a scope inside a patient during a surgical procedure may include wetting the sponge, retracting the sponge, advancing a cannula into the patient including the device, deploying the sponge, and contacting the lens with the outer surface of the sponge to clean the lens.

The sponge may be applied to clean the lens using a side of the sponge, and end of the sponge, or in any configuration based on an application or surgery. Thus, the end of tip of the sponge may also include a cleaning surface.

Example devices described herein may be of various configurations and sizes, and thus, may be used for cleaning various instruments within a body cavity, including but not limited to, laparoscopes, endoscopes, or other instruments including lenses or cameras.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

What is claimed is:

1. A handle for a medical device, the handle being coupled to a proximal end of the device, the handle comprising:
    a top comprising a first end and a second end;
    a first top side coupled to the first end of the top via a first corner hinge;
    a second top side coupled to the second end of the top via a second corner hinge;
    a first bottom side coupled to the first top side via a first side hinge;
    a second bottom side coupled to the second top side via a second side hinge;
    a bottom coupled to the first bottom side via a third corner hinge and coupled to the second bottom side via a fourth corner hinge;
    an actuation member positioned between the top and the bottom; and
    a rod coupled to the actuation member, wherein actuation of the handle causes the actuation member to drive the rod.

2. The handle of claim 1, further comprising:
    a top side stopper on an inner surface of each of the first top side and the second top side; and
    a bottom side stopper on an inner surface of each of the first bottom side and the second bottom side.

3. The handle of claim 2, wherein the handle is configured to be compressed an amount to an extent such that the top side stopper on the inner surface of each of the first top side and the second top side contact the bottom side stopper on the inner surface of each of the first bottom side and the second bottom side.

4. The handle of claim 2, wherein an amount of rotation enabled by the first corner hinge, the second corner hinge, the third corner hinge, the fourth corner hinge, the first side hinge, and the second side hinge is limited due to contact of the top side stopper on the inner surface of each of the first top side and the second top side with the bottom side stopper on the inner surface of each of the first bottom side and the second bottom side.

5. The handle of claim 2, further comprising:
    a top middle stopper on an inner surface of the top; and
    a bottom middle stopper on an inner surface of the bottom.

6. The handle of claim 5, wherein the handle is configured to be compressed an amount to an extent such that the top side stopper on the inner surface of each of the first top side and the second top side contact the top middle stopper on the inner surface of the top and such that the bottom side stopper on the inner surface of each of the first bottom side and the second bottom side contact the bottom middle stopper on the inner surface of the bottom.

7. The handle of claim 5, wherein the handle is configured to be compressed an amount to an extent such that the top middle stopper contacts the bottom middle stopper.

8. The handle of claim 5, wherein an amount of rotation enabled by the first corner hinge, the second corner hinge, the third corner hinge, the fourth corner hinge, the first side hinge, and the second side hinge is limited due to contact of the top side stopper on the inner surface of each of the first top side and the second top side with the top middle stopper on the inner surface of the top and contact of the bottom side stopper on the inner surface of each of the first bottom side and the second bottom side with the bottom middle stopper on the inner surface of the bottom.

9. The handle of claim 5, wherein an amount of rotation enabled by the first corner hinge, the second corner hinge, the third corner hinge, the fourth corner hinge, the first side hinge, and the second side hinge is limited due to contact of the top middle stopper with the bottom middle stopper.

10. The handle of claim 1, wherein the first bottom side and the first top side are rotatable about a first axis via the first side hinge, and the second bottom side and the second top side are rotatable about the first axis via the second side hinge.

11. The handle of claim 10, wherein the first side hinge and the second side hinge enable rotation of the first bottom side and the first top side about the first axis and the second bottom side and the second top side about the first axis at angles between 45° to 180°.

12. The handle of claim 11, wherein
    the first top side and the top are rotatable about a second axis via the first corner hinge;
    the second top side and the top are rotatable about a third axis via the second corner hinge;
    the first bottom side and the bottom are rotatable about the second axis via the third corner hinge; and the second bottom side and the bottom are rotatable about the third axis via the fourth corner hinge, and wherein the second axis and the third axis are parallel, and the first axis is perpendicular to the second axis and the third axis.

13. The handle of claim 12, wherein
the first corner hinge enables rotation of the first top side and the top at angles between 90° to 180°;
the second corner hinge enables rotation of the second top side and the top at angles between 90° to 180°;
the third corner hinge enables rotation of the first bottom side and the bottom at angles between 90° to 180°; and
the fourth corner hinge enables rotation of the second bottom side and the bottom at angles between 90° to 180°.

14. The handle of claim 13, wherein the top, the first top side, the second top side, the first bottom side, the second bottom side, and the bottom are configured to be a rectangular shape with the first side hinge and the second side hinge configured to be at an angle of 180° and each of the first corner hinge, the second corner hinge, the third corner hinge, and the fourth corner hinge configured to be at an angle of 90°.

15. The handle of claim 13, wherein the top, the first top side, the second top side, the first bottom side, the second bottom side, and the bottom are configured to be a hexagonal shape with the first side hinge and the second side hinge configured to be at an angle of 60° and each of the first corner hinge, the second corner hinge, the third corner hinge, and the fourth corner hinge configured to be at an angle of 150°.

16. The handle of claim 1, wherein the top, the first top side, the second top side, the first bottom side, the second bottom side, and the bottom are configured to be a rectangular shape.

17. The handle of claim 1, wherein the top, the first top side, the second top side, the first bottom side, the second bottom side, and the bottom are configured to be a hexagonal shape.

18. The handle of claim 1, wherein the top, the bottom, the first top side, the second top side, the first bottom side, the second bottom side, the first corner hinge, the second corner hinge, the third corner hinge, the fourth corner hinge, the first side hinge, and the second side hinge are one integral component.

19. The handle of claim 1, wherein the top and the bottom are the same length.

20. The handle of claim 1, wherein the first top side, the second top side, the first bottom side, and the second bottom side are the same length.

21. The handle of claim 1, wherein the first top side, the second top side, the first bottom side, and the second bottom side have a larger length than a length of the top.

22. The handle of claim 1, wherein the first side hinge and the second side hinge have a greater amount of possible rotation than the first corner hinge, the second corner hinge, the third corner hinge, and the fourth corner hinge.

23. The handle of claim 1, wherein the first corner hinge, the second corner hinge, the third corner hinge, the fourth corner hinge, the first side hinge, and the second side hinge are configured to enable compression of the handle causing the top and the bottom to move toward each other resulting in actuation of the handle.

24. A handle for a medical device, the handle being coupled to a proximal end of the device, the handle comprising:
a top;
a bottom;
a first side and a second side coupled to the top and the bottom via corner hinges, and wherein the first side and the second side include side hinges;
an actuation member positioned between the top and the bottom; and
a rod coupled to the actuation member, wherein actuation of the handle causes the actuation member to drive the rod.

25. The handle of claim 24, wherein
wherein the corner hinges and the side hinges enable actuation of the handle into a first position resulting in the handle being configured in a hexagonal shape, and
wherein the corner hinges and the side hinges enable actuation of the handle into a second position resulting in the handle being configured in a rectangular shape.

26. The handle of claim 24, wherein the side hinges enable the first side and the second side to bend about an axis at angles between 45° to 180°.

27. The handle of claim 24, wherein
the corner hinges enable rotation of the first side and the top, and the second side and the top at angles between 90° to 180°, and
the corner hinges enables rotation of the first side and the bottom, and the second side and the bottom at angles between 90° to 180°.

28. The handle of claim 24, wherein the top, the first side, the second side, and the bottom are configured to be a rectangular shape with the side hinges configured to be at an angle of 180° and the corner hinges configured to be at an angle of 90°.

29. The handle of claim 24, wherein the top, the first side, the second side, and the bottom are configured to be a hexagonal shape with the side hinges configured to be at an angle of 60° and the corner hinges configured to be at an angle of 150°.

30. A handle for a laparoscopic lens internal cleaning device, the handle being coupled to a proximal end of the device, the handle comprising:
an actuation member positioned between a top and a bottom; and
a rod coupled to the actuation member,
wherein actuation of the handle into a first position resulting in the handle being configured in a hexagonal shape causes the actuation member to drive the rod for deployment of a sponge from the device, and
wherein actuation of the handle into a second position resulting in the handle being configured in a rectangular shape causes the actuation member to pull the rod for retraction of the sponge into the device.

31. The handle of claim 30, further comprising:
a top comprising a first end and a second end;
a first top side coupled to the first end of the top via a first corner hinge;
a second top side coupled to the second end of the top via a second corner hinge;
a first bottom side coupled to the first top side via a first side hinge;
a second bottom side coupled to the second top side via a second side hinge; and
a bottom coupled to the first bottom side via a third corner hinge and coupled to the second bottom side via a fourth corner hinge,
wherein the top, the first top side, the second top side, the first bottom side, the second bottom side, and the bottom are configured to be a rectangular shape with the first side hinge and the second side hinge configured to be at an angle of 180° and each of the first corner hinge, the second corner hinge, the third corner hinge, and the fourth corner hinge configured to be at an angle of 90°, and
wherein the top, the first top side, the second top side, the first bottom side, the second bottom side, and the bottom are configured to be a hexagonal shape with the first side hinge and the second side hinge configured to be at an angle of 60° and each of the first corner hinge, the second corner hinge, the third corner hinge, and the fourth corner hinge configured to be at an angle of 150°.

* * * * *